(12) United States Patent
Tsang et al.

(10) Patent No.: US 6,630,580 B2
(45) Date of Patent: *Oct. 7, 2003

(54) SILYL AND HEPARIN COMPOSITIONS

(75) Inventors: Ray Tsang, Salt Lake City, UT (US); Shigemasa Osaki, Sandy, UT (US)

(73) Assignee: InnerDyne, Inc., Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/047,118

(22) Filed: Jan. 14, 2002

(65) Prior Publication Data

US 2002/0115836 A1 Aug. 22, 2002

Related U.S. Application Data

(63) Continuation of application No. 09/629,059, filed on Jul. 31, 2000, now Pat. No. 6,342,591, which is a continuation-in-part of application No. 09/399,119, filed on Sep. 20, 1999, now abandoned, which is a continuation of application No. 09/159,276, filed on Sep. 22, 1998, now Pat. No. 5,955,588.

(51) Int. Cl.[7] ..................... C08B 37/10; A61K 31/727; A01N 1/00; A61M 5/32
(52) U.S. Cl. ..................... 536/21; 514/56; 523/112; 604/266; 427/2.1; 427/2.24; 427/2.25; 427/2.3
(58) Field of Search .................. 536/21; 514/56; 523/112; 604/266; 427/2.1, 2.24, 2.25, 2.3

(56) References Cited

U.S. PATENT DOCUMENTS

| | | | |
|---|---|---|---|
| 3,522,346 A | 7/1970 | Chang | 424/35 |
| 3,618,613 A | 11/1971 | Schulte | 128/348 |
| 3,810,781 A | 5/1974 | Eriksson et al. | 117/47 A |
| 4,046,725 A | 9/1977 | Pusineri | 260/9 |
| 4,073,723 A | 2/1978 | Swank et al. | 210/23 R |
| 4,118,485 A | 10/1978 | Eriksson et al. | 424/183 |
| 4,219,520 A | 8/1980 | Kline | 264/129 |
| 4,254,180 A | 3/1981 | Kline | 428/323 |
| 4,265,927 A | 5/1981 | Ericksson et al. | 427/2 |
| 4,378,224 A | 3/1983 | Nimni et al. | 8/94.11 |
| 4,448,691 A | 5/1984 | Davis | 210/656 |
| 4,779,641 A | 10/1988 | Charm et al. | 137/238 |
| 4,833,200 A | 5/1989 | Noishiki et al. | 525/54.2 |
| 4,865,870 A | 9/1989 | Hu et al. | 427/2 |
| 4,871,357 A | 10/1989 | Hsu et al. | 604/266 |
| 4,871,437 A | 10/1989 | Marschman et al. | 204/291 |
| 4,921,483 A | 5/1990 | Wijay et al. | 604/96 |
| 5,019,096 A | 5/1991 | Fox, Jr. et al. | 623/1 |
| 5,047,020 A | 9/1991 | Hsu | 604/266 |
| 5,067,491 A | 11/1991 | Taylor, II et al. | 128/748 |
| 5,069,899 A | 12/1991 | Whitbourne et al. | 424/56 |
| 5,135,516 A | 8/1992 | Sahatjian et al. | 604/265 |
| 5,308,617 A | 5/1994 | Halluin | 424/94.64 |
| 5,334,379 A | 8/1994 | Pillai et al. | 424/85.2 |
| 5,336,518 A | 8/1994 | Narayanan et al. | 623/1 |
| 5,338,770 A | 8/1994 | Winters et al. | 523/112 |
| 5,383,927 A | 1/1995 | De Goicoechea et al. | 623/1 |
| 5,391,580 A | 2/1995 | Douglas et al. | 521/27 |
| 5,463,010 A | 10/1995 | Hu et al. | 528/25 |
| 5,541,167 A | 7/1996 | Hsu et al. | 514/56 |
| 5,650,234 A | 7/1997 | Dolence et al. | 428/447 |
| 5,955,588 A | 9/1999 | Tsang et al. | 536/21 |

FOREIGN PATENT DOCUMENTS

GB 863235 3/1961

OTHER PUBLICATIONS

Nagasawa, K. et al. "[43] De–N–Sulfation" Methods in Carbohydrate Chemistry vol. VIII, pp. 291–294 (1980).
Levy, L. et al. "Chemical and Pharmacological Studies of N–Resulfated Heparin (27372)." Proc. Soc. Expt. Biol. and Med. (1962) 901–905.
Data Sheet #172, Polysciences, Inc. "TDMAC–Heparin Coatings for Preparing Antithrombogenic Plastic Surfaces." Mar., 1991.
Shaklee, P.N. et al. "Hydrazinolysis of Heparin and Other Glycosaminoglycans." Biochem Journal (1984) 217, 187–197.
Inoue, Y. et al. "Depolymerization of Heparin with Diazomethane, Structure of N,O–Methylated, Even–Numbered Oligsaccharides Produced by B–Eliminative Cleavage of the 2–Amino–2–Deoxyglycosylic Linkage." Carbohydrate Research 131 (1984) 285–300.
Gitel, S.N. et al. "Preparation and Identification of a Population of Antibodies that Recognize Carbodiimide–Modified Heparin." Blood, vol. 65, No. 4 (Apr. 1985) 902–911.
Kim, Y.J. et al. "Thermal and Structural Analysis of Heparin–PEO–PDMS–PEO–Heparin Pentablock Copolymers." Journal of Applied Polymer Science, vol. 54 (1994) 1863–1872.

Primary Examiner—Kathleen K. Fonda
(74) Attorney, Agent, or Firm—Stephen A. Slusher; Peacock, Myers & Adams, PC (57) ABSTRACT

The present invention provides an anti-thrombogenic and cellular-adhesion coating composition for blood-contacting surfaces. The coating comprises a covalent complex of from 1 to 30 hydrophobic silyl moieties of Formula I:

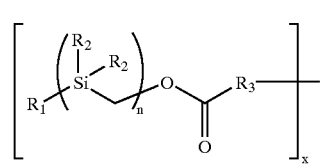

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, directly bound to a heparin molecule via covalent bonding, with an adhesive molecule directly bound to the heparin molecule. In one embodiment, the coating comprises benzyl-(1,2 dimethyl)disilyl heparin, wherein an adhesive molecule, such as fibronectin, is bound to the heparin.

15 Claims, 2 Drawing Sheets

SILYL AND HEPARIN COMPOSITIONS

CROSS REFERENCE TO RELATED APPLICATIONS

This application is a continuation of U.S. patent application Ser. No. 09/629,059, entitled Amphipathic Coating for Modulating Cellular Adhesion Composition and Methods, to Paul O. Zamora, Shigemasa Osaki and Ray Tsang, filed on Jul. 31, 2000, now U.S. patent No. 6,342,591. issued Jan. 29, 2002, which is a continuation-inpart application of U.S. patent application Ser. No. 09/399,119, entitled Non-Thrombogenic Coating Compositions and Methods for Using Same, to Ray Tsang and Shigemasa Osaki filed on Sep. 20, 1999, now abandoned, which is a continuation patent application of U.S. patent application Ser. No. 09/159,276, filed on Sep. 22, 1998, now U.S. Pat. No. 5,955,588, entitled Non-Thrombogenic Coating Compositions and Methods for Using Same, to Ray Tsang and Shigemasa Osaki, and the specification of each of the foregoing is incorporated herein by reference.

BACKGROUND OF THE INVENTION

1. Field of the Invention (Technical Field)

The present invention relates to coatings and methods of use of non-thrombogenic compositions for selectively inhibiting and promoting cellular attachment, including a silyl-heparin-fibronection composition for promoting cellular attachment.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Heparin is naturally present in various tissues, including liver and lung, as well as the luminal surface of endothelial cells. It is composed of repeating units of D-glucuronic acid and D-glucosamine, both sulfated, in a 1,4-α linkage. Heparin is an anticoagulant, and it has been reported that on the surface of endothelial cells heparin minimizes fibrin accumulation. When administered as a parenteral drug, heparin activates anti-thrombin III, which leads to inactivation of thrombin and ultimately systemic inhibition of fibrin formation.

A number of medical devices that come in contact with blood have been coated with heparin with the goal of taking advantage of its thrombo-resistant nature. Stents, catheters, oxygenator fibers, and cardiac bypass circuits are examples of medical devices that have been coated with heparin (Niimi et al., *Anesth Analg* 89:573–9, 1999; Inui et al., *Artif Organs*, 23:1107–12, 1999). Various strategies have been developed to attach heparin to medical polymer surfaces including chemical conjugation (Siefert et al., *J Biomater Sci Polym Ed,* 7:277–87, 1995), plasma glow discharge methods (Kim et al., *Biomaterials,* 21:121–30, 2000), the combination of both, and hydrophobic interaction as described herein (U.S. Pat. No. 5,955,588).

Heparin has a number of other biological actions related to its presence in the extracellular matrix. In the extracellular matrix, heparin and its chemical relative heparan sulfate is complexed into a scaffolding onto which cells attach. In this scaffolding, heparin is bound by fibronectin and other adhesive molecules, which in turn bind to cells. Extracellular matrix heparin and heparin sulfate also act as reservoirs for growth factors, not only binding growth factors but also protecting them from protease degradation. Fibroblast growth factor (FGF), platelet-derived growth factor (PDGF), and bone morphogenic protein (BMP) are examples of growth factors that complex to heparin.

The ability of heparin to bind adhesive molecules and growth factors has lead to a number of efforts to use heparin complexes to improve implantable medical device surfaces by providing surfaces to which cells can attach and migrate. Other researchers have explored direct coatings of fibronectin, and peptides and peptide mimetics derived from fibronectin, with the goal of increasing cell attachment (Walluscheck et al., *Eur J Vasc Endovasc Surg,* 12:321–30, 1996; Boxus et al., *J Bioorg Med Chem,* 6:1577–95,1998; Tweden et al., *J. Heart Valve Dis,* 4 Suppl 1:S90-7, 1995). Vascular grafts, for example, would be improved by a surface that supports the growth of endothelial cells. Current vascular grafts of polytetrafluoroethylene and polyethylene terephthalate do not support endothelization, and consequently patients must be maintained on long-term anti-platelet therapy.

Fibronectins function as adhesive, ligand molecules interacting with specific receptors on the cell surface. Cells types that attach to fibronectin include fibroblasts, endothelial cells, smooth muscle cells, osteoblasts, and chondrocytes.

Other investigators have used heparin/fibronectin complexes to provide cell adhesion to polymeric surfaces. For example, heparin-albumin conjugates have been immobilized on carbon dioxide gas plasma-treated polystyrene (Bos et al., *J. Biomed Mater Res,* 47:279–91, 1999) and complexed to fibronectin. The fibronectin on these surfaces increased the attachment of endothelial cells. Bos et al. (*Tissue Eng* 4:267–79, 1998; *J Biomed Mater Res* 47:279–91, 1999) reported that endothelial cells grew to confluency on $CO_2$ gas plasma-treated polystyrene coated with an albumin-heparin conjugate. Ishihara et al. (*J Biomed Mater Res,* 50: 144–152, 2000) reported that a heparin-conjugated polystyrene promoted cell attachment of fibroblasts, smooth muscle cell and endothelial cells. The fibroblasts grown on heparin-conjugated polystyrene had growth rates at least comparable to fibronectin-coated, gelatin-coated, or tissue culture-treated media.

A simple method of efficiently complexing fibronectin or other adhesive molecules, including derivatives or mimics of the foregoing, to a heparin complex would have wide applicability for attaching cells to prostheses, including vascular grafts, bone and cartilage implants, nerve guides and the like. Particularly needed is a method and composition permitting use of a wide variety of adhesive molecules, including fibronectin, laminin and the like, as part of a coating for implantable medical devices. There remains a need in the art for coating compositions for implantable medical devices that promote cellular attachment, and further wherein cellular attachment can be modulated by the quantity of adhesive molecule, and which can be applied simply and easily with no specialized equipment or techniques.

SUMMARY OF THE INVENTION
(DISCLOSURE OF THE INVENTION)

The present invention provides an amphipathic cell-attachment coating composition for medical device surfaces, which composition includes a covalent complex of from 1 to 30 hydrophobic silyl moieties of Formula I:

wherein

R$_1$ is an C$_{1-18}$ alkyl or C$_{6-32}$ aryl group, each R$_2$ is independently selected from the group consisting of C$_{1-18}$ alkyl and C$_{6-32}$ aryl R$_3$ is N or O, and n is a number from 1 to 10 directly bound to sodium heparin via covalent bonding, with an adhesive molecule directly bound to the sodium heparin. The hydrophobic silyl moieties may be bound to the surfaces via hydrophobic bonding interactions. Further, the complex can include from 2 to 25 hydrophobic silyl moieties covalently bound to one heparin molecule. In Formula I, R$_1$ can be benzyl and R$_2$ can be an alkyl. In a preferred embodiment, the complex is [benzyl-bis(dimethylsilylmethyl)]-(N-heparinyl)-carbamate or [benzyl-tris(dimethylsilylmethyl)]-(N-heparinyl)-carbamate. In a preferred embodiment, the adhesive molecule is fibronectin; in alternative embodiments, the adhesive molecule may be laminin, vitronectin, thrombospondin, gelatin, polylysine, polyornithine, peptide polymers containing adhesive sequences and heparin binding sequences, sulfated complex carbohydrates, dextran sulfate, growth hormones, cytokines, lectins, or peptidic polymers thereof.

The invention further provides a non-thrombogenic medical device for cellular attachment, including surfaces for contacting blood, which surfaces have coated thereon an non-thrombogenic coating composition comprising a covalent complex of from 1 to 30 hydrophobic silyl moieties of Formula I:

wherein

R$_1$ is an C$_{1-18}$ alkyl or C$_{6-32}$ aryl group, each R$_2$ is independently selected from the group consisting of C$_{1-18}$ alkyl and C$_{6-32}$ aryl, R$_3$ is N or O, and n is a number from 1 to 10 directly bound to heparin via covalent bonding, with an adhesive molecule directly bound to the heparin. The hydrophobic silyl moieties may be bound to the coated surfaces via hydrophobic bonding interactions. Further, the complex can include from 2 to 25 hydrophobic silyl moieties covalently bound to one heparin molecule. In Formula I, R$_1$ can be benzyl and R$_2$ can be an alkyl. In a preferred embodiment, the complex is [benzyl-bis (dimethylsilylmethyl)]-(N-heparinyl)-carbamate or [benzyl-tris(dimethylsilylmethyl)]-(N-heparinyl)-carbamate. In a preferred embodiment, the adhesive molecule is fibronectin; in alternative embodiments, the adhesive molecule may be laminin, vitronectin, thrombospondin, gelatin, polylysine, polyornithine, peptide polymers containing adhesive sequences and heparin binding sequences, sulfated complex carbohydrates, dextran sulfate, growth hormones, cytokines, lectins, or peptidic polymers thereof. The devices of this invention include blood gas exchange devices, blood filters, artificial blood vessels, artificial valves, prosthetics, blood shunts, catheters, bone replacements, cartilage replacements and nerve growth guides.

In yet another embodiment, the invention provides a method for rendering a tissue- or blood-contacting surfaces of a medical device resistant to fibrin accumulation while promoting cellular adhesion, which method includes coating the surfaces with an non-thrombogenic coating composition comprising a covalent complex of from 1 to 30 hydrophobic silyl moieties of Formula I:

wherein

R$_1$ is an C$_{1-18}$ alkyl or C$_{6-32}$ aryl group, each R$_2$ is independently selected from the group consisting of C$_{1-18}$ alkyl and C$_{6-32}$ aryl, R$_3$ is N or O, and n is a number from 1 to 10 directly bound to heparin via covalent bonding, and attaching to the heparin an adhesive molecule. In this method, the hydrophobic silyl moieties can be bound to the surfaces via hydrophobic bonding interactions. From 2 to 25 hydrophobic silyl moieties can be covalently bound to one heparin molecule. In a preferred embodiment, R$_1$ is benzyl and R$_2$ is an alkyl. In preferred embodiments, the complex is [benzyl-bis (dimethylsilylmethyl)]-(N-heparinyl)-carbamate or [benzyl-tris(dimethylsilylmethyl)]-(N-heparinyl)-carbamate. The method can further include the step of solubilizing the complex in a solvent prior to the step of coating the surface. In one embodiment, the step of coating the surfaces includes dipping the surface into the coating composition including the complex. In another embodiment, the step of coating the surface includes pumping the coating composition including the complex onto the surface. In a preferred embodiment of this method, the adhesive molecule is fibronectin; in alternative embodiments, the adhesive molecule may be laminin, vitronectin, thrombospondin, gelatin, polylysine, polyornithine, peptide polymers containing adhesive sequences and heparin binding sequences, sulfated complex carbohydrates, dextran sulfate, growth hormones, cytokines, lectins, or peptidic polymers thereof. The method can also include the step of solubilizing the adhesive molecule in a solvent prior to the step of attaching the adhesive molecule. The step of attaching the adhesive molecule includes dipping the surface coated with the complex into a solubilized adhesive molecule composition. Alternatively, the step of attaching the adhesive molecule includes pumping the solubilized adhesive molecule composition onto a surface coated with the complex.

A primary object of the present invention is to provide an amphipathic heparin-fibronectin coating composition for implantable medical devices, which promotes cellular attachment.

A further objective of the invention is to provide a coating the composition of which can be varied, such that absent an adhesion molecule the coating inhibits fibrin deposition, but when the coating includes an adhesion molecule, the coating promotes cellular attachment and cell growth.

A further object of the invention is to provide coating compositions utilizing fibronectin, derivations of fibronectin, peptide mimics of fibronectin, laminin, vitronectin, thrombospondin, gelatin, collagen and subtypes thereof, gelatin, polylysine, polyornithine, and other adhesive molecules or derivatives or mimics of other adhesive molecules.

A further object of the present invention is to provide a cost effective and commercially feasible method for coating polymeric medical devices, including biodegradable medical devices, with a non-thrombogenic coating that inhibits cell attachment.

A further object of the present invention is to provide a cost effective and commercially feasible method for coating polymeric medical devices, including biodegradable medical devices, with a coating that resists fibrin accumulation and promotes cell attachment and growth utilizing a complex with an adhesive molecule, including fibronectin, peptide mimics of fibronectin, laminin, vitronectin, thrombospondin, gelatin, collagen and subtypes thereof, gelatin, polylysine, polyornithine, and other adhesive molecules or derivatives or mimics of other adhesive molecules.

A primary advantage of the present invention is that it provides for coating medical devices of complex geometries and surfaces with a durable and low-cost coating that promotes uniform cell growth and attachment.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIGS. 2A and B are plots of the absorbance resulting from heparin and fibronectin added in serial doubling dilutions measured using assays.

DESCRIPTION OF THE PREFERRED EMBODIMENTS

Best Modes for Carrying Out the Invention

The present invention relates to new non-thrombogenic, cell-attachment coating compositions. According to the compositions of the present invention, hydrophobic moieties are covalently bound to a heparin molecule to form a covalent, amphipathic complex which may used singly or in combination with adhesion molecules to promote cell attachment.

As a first aspect, the present invention provides an amphiphatic coating that resists fibrin accumulation and inhibits cell attachment. The coating comprises a covalent complex of from 1 to 30 hydrophobic silyl moieties of Formula I:

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, and n is a number from 1 to 10, directly bound to a heparin molecule via covalent bonding, with an adhesive molecule complexed by affinity interaction to the heparin.

As a second aspect, the present invention provides medical devices coated with the moieties of Formula I that inhibits fibrin accumulation and cellular adhesion, comprising surfaces for contacting blood and other surfaces where cellular attachment is not desired. The fibrin-resistant and cellular-adhesion resistant coating composition comprises a covalent, amphipathic complex of from 1 to 30 hydrophobic silyl moieties of Formula I directly bound to a heparin molecule via covalent bonding but without an adhesive molecule.

As a third aspect, the present invention provides a fibrin-resistant medical device that promotes surface cellular adhesion, comprising surfaces for contacting blood, cells, tissues, or other fluids. The blood- or cell-contacting surfaces have coated thereon a fibrin-resistant and cellular-adhesion coating composition. The fibrin resistant and cellular-adhesion coating composition includes a covalent, amphipathic complex of from 1 to 30 hydrophobic silyl moieties of Formula I directly bound to a heparin molecule via covalent bonding, wherein an adhesive molecule, including but not limited to fibronectin, is complexed by affinity interaction to the heparin.

As a fourth aspect, the present invention provides a method for rendering blood- and cell-contacting surfaces of a medical device resistant to fibrin accumulation while promoting cellular adhesion. The method comprises coating the surfaces with an anti-fibrin coating composition. The composition comprises a covalent complex of from 1 to 30 hydrophobic silyl moieties of Formula I directly bound to a heparin molecule via covalent bonding. Thereafter, an adhesion molecule, such as fibronectin, is bound by affinity interaction to the heparin.

As a fifth aspect, the present invention provides a covalent complex of Formula II:

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and x is a number from 1 to 30.

These and other aspects of the present invention are described further in the description of the preferred embodiment and examples of the invention which follow.

Description of the Preferred Embodiment

Unless otherwise defined, all technical and scientific terms employed herein have their conventional meaning in the art. As used herein, the following terms have the means ascribed to them.

"Alkyl" refers to linear branched or cyclic, saturated or unsaturated $C_{1-18}$ hydrocarbons such as methyl, ethyl, ethenyl, propyl, propenyl, iso-propyl, butyl, iso-butyl, t-butyl, pentyl, cyclopentyl, hexyl, cyclohexyl, octyl, and the like.

"Aryl" refers to unsaturated $C_{6-32}$ hydrocarbon rings that may be substituted from 1–5 times with alkyl, halo, or other aryl groups. Aryl also includes bicyclic aryl groups. Specific examples of aryl groups include but are not limited to phenyl, benzyl, dimethyl phenyl, tolyl, methyl benzyl, dimethyl benzyl, trimethyl phenyl, ethyl phenyl, ethyl benzyl, and the like.

"Adhesive molecule" refers molecules which promote cellular attachment, adhesion or growth, including fibronectin, laminin, vitronectin, thrombospondin, heparin-binding domains, and heparan sulfate binding domains, as well as synthetic polymers of amino acids containing adhesive sequences derived from any of the foregoing. This includes, without limitation, peptides or polypeptides containing the amino acids with the single letter codes RGD, IKVAV, YIGSR, and the like. Adhesive molecules also include lectins that bind to heparin and carbohydrate moieties on the cell surface.

"Heparin" as used herein includes complex carbohydrates or mimetics of complex carbohydrates with properties similar to those of heparin, including heparan sulfate, dextran, dextran sulfate, chondroitin sulfate, dermatan sulfate, and the like.

Heparin Coating Compositions

The heparin coating compositions of the present invention comprise a covalent complex of one or more hydrophobic silyl moieties with heparin. Heparin is a mixture of variably sulfated polysaccharide chains composed of repeating units of D-glucosamine and either L-iduronic or D-glucuronic acids.

Any suitable form of heparin may be employed in the reaction. Several salts of heparin and heparin derivatives are known in the art. For example, conventional salts of heparin include sodium heparin, calcium heparin, magnesium heparin, and potassium heparin. Heparin derivatives include, but are not limited to ammonium heparin, benzalkonium heparin, and the like. Sodium heparin is one preferred form of heparin for preparing the covalent complexes according to the present invention. For the sake of simplicity, the term "heparin molecule" refers to any of known forms of heparin including all salts and derivatives of heparin.

The silyl moiety is represented by the general Formula I:

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, and n is a number from 1 to 10. As will be apparent to those skilled in the art, $R_3$ is an N or O atom on the heparin molecule, and the unoccupied bond from $R_3$ signifies the attachment of the silyl moiety to the heparin molecule. Thus, the hydrophobic silyl moiety is capable of attachment to the heparin molecule at either an O atom of an alcohol (i.e., hydroxyl) or a N atom of an amine.

Heparin comprises many repeating units containing amine and hydroxyl functional groups which can be the site for attachment of the hydrophobic silyl moiety to the heparin molecule. Accordingly, one embodiment of the present invention contemplates the attachment of more than 1 hydrophobic silyl moiety to a single heparin molecule. As many as 30 hydrophobic silyl moieties of Formula I or more, and as few as 1 hydrophobic silyl moiety may be attached to a single heparin molecule to achieve the covalent complex employed in the heparin coating compositions of the present invention. In one embodiment of the present invention, between 2 and 25 hydrophobic silyl moieties are attached to a single heparin molecule. In one embodiment, between 5 and 20 hydrophobic silyl moieties are attached to a single heparin molecule. In one embodiment, between 7 and 15 hydrophobic silyl moieties are attached to a single heparin molecule. In one preferred embodiment, 7 or 8 hydrophobic silyl moieties are attached to a single heparin molecule. In another preferred embodiment 12 hydrophobic silyl moieties are attached to a single heparin molecule.

In those embodiments wherein more than one hydrophobic silyl moiety is attached to a single heparin molecule, the hydrophobic silyl moieties may be attached either through the amine of heparin (e.g., where $R_3$ is N) or through the hydroxyl group of heparin (e.g., wherein $R_3$ is O). In other words, some of they hydrophobic silyl moieties may be attached to the heparin molecule via bonding at the amine groups of heparin, while other hydrophobic silyl moieties are attached to the heparin molecule via bonding at the hydroxyl groups of heparin. It is also possible for all of the hydrophobic silyl moieties to be consistently attached to heparin via one or the other of the amine (e.g., $R_3$ in all hydrophobic silyl moieties is N) or the alcohol (e.g., $R_3$ in all hydrophobic silyl moieties is O).

The bonds between the hydrophobic silyl moieties and the heparin molecule which effect the attachment of the moieties to the molecule are covalent bonds. Thus, the coating compositions of the present invention do not rely upon ionic interactions between heparin and the hydrophobic moiety. Rather, the hydrophobic moieties are bonded to the heparin molecule by covalent bonding through either the amine or hydroxyl groups (or possibly a combination of both amine and hydroxyl groups when two or more hydrophobic silyl moieties are attached a single heparin molecule). Because the hydrophobic silyl moiety is bound to the heparin molecule through covalent bonding, the present invention overcomes one weakness of conventionally known heparin coatings. Specifically, the problem of heparin leaching from the coating as a result of the breaking of the ionic bond between heparin and the group which attaches heparin to the surface is overcome by avoiding reliance upon ionic bonding interactions between heparin and the binding group. In the present invention, the covalent bonds between the hydrophobic silyl moieties and the heparin molecule in the coating composition are not disrupted by the presence of ionic species in the blood with which the coated surface will come into contact. The data demonstrate that this process of covalent modification also does not lead to detrimental loss of heparin activity as monitored by a Factor Xa/antithrombin III chromogenic substrate assay on the surface of target substrates.

The covalent complex according to the present invention can be prepared according to the following Scheme 1.

ducted at temperatures of about 10° C. or less. The reaction is carried out for a sufficient period of time to yield about 80–90% product. Typically the reaction is conducted over a period of from about 2 to about 24 hours.

First intermediates wherein n is 2 or higher can be produced using a Grignard Reaction involving the reaction of the first intermediate wherein n is 1 with $ClSi(R_2)_2CH_2Cl$. This Grignard reaction can be repeated any number of times to achieve the desired value for n in the first intermediate. The reaction is carried out in the presence of a catalytic amount of iodine and THF.

The first intermediate (wherein n is 1–10) is converted to the second intermediate, $R_1(Si(R_2)_2CH_2)_nOH$, by reacting the first intermediate with potassium acetate (KOAc) in dimethyl formamide (DMF), at a temperature of above about 120° C., and preferably about 135° C. for between 12 and 24 hours. The product of this reaction is then reacted with sodium methoxide (NaOMe) in methanol (MeOH) under reflux for about 2 hours to achieve the second intermediate.

Scheme 1 wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and x is a number from 1 to 30.

Generally, the first intermediate, $R_1(Si(R_2)_2CH_2)_nCl$ wherein n is 1, is produced by reacting an alkyl or aryl magnesium chloride with a chloro(chloromethyl)-dialkyl silane or chloro(chloromethyl)diaryl silane in the presence of tetrahydrofuran (THF). The alkyl or aryl magnesium chlorides used as starting materials are commercially available, and include, for example benzyl magnesium chloride. The chloro(chloromethyl)dialkyl silane or chloro(chloromethyl)diaryl silanes are also commercially available and include, for example chloro(chloromethyl)dimethyl silane. The reaction is exothermic, and is typically con- The second intermediate is converted to the last intermediate, $R_1(Si(R_2)_2CH_2)_nOCO_2N(COCH_2)_2$, by a two-step reaction process. In the first step, the second intermediate is reacted with triphosgene and sodium carbonate in methylene chloride at a temperature of less than 10° C., and preferably about 0° C. The product of this reaction is reacted with N-hydroxysuccinimide and triethylamine ($Et_3N$) in methylene chloride at a temperature of less than 10° C., and preferably about 0° C.

The final intermediate is covalently conjugated to heparin by reacting heparin with the final intermediate in a suitable solvent (e.g., water/dimethyl formamide) at a pH of about 8.0 to 9.0, and preferably about 8.5. The pH of the reaction is controlled by the addition of base such as sodium hydroxide, as needed.

Using these general methods, the covalent complexes of the present invention can be produced.

The covalent complexes have the general Formula III:

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and x is a number from 1 to 30.

Preferred complexes include those complexes wherein $R_1$ of the hydrophobic silyl moiety is aryl. In one preferred embodiment, $R_1$ is benzyl. In one preferred embodiment, each $R_2$ is alkyl. In one particularly preferred embodiment, each $R_2$ is selected from the group consisting of methyl, ethyl, propyl, and isopropyl, particularly methyl. In one preferred embodiment, n is a number from 2 to 3.

Specific examples of covalent complexes according to the present invention include but are not limited to [benzyl-bis(dimethylsilylmethyl)]-(N-heparinyl)-carbamate, [benzyl-tris(dimethylsilylmethyl)]-(N-heparinyl)-carbamate, and dodecyl[benzyl-bis(dimethylsilylmethyl)]-(N-heparinyl)-carbamate. Although these three specific covalent complexes are examples of currently preferred covalent complexes having the general Formula II above, other specific examples of such complexes will be apparent to those skilled in the art and are contemplated by the instant invention.

The silyl-heparin coatings of the present invention comprise the covalent complexes described above. In addition to the covalent complex, the coating composition may also include one or more solvents which facilitate the processes of applying the composition to the surface. Suitable solvents will be those which at least partially solubilize the covalent complex and which do not interfere with the anti-thrombogenic activity of heparin. Examples of solvents which may be employed in the coating compositions of the present invention include but are not limited to aqueous solvents, alcohols, nitriles, amides, esters, ketones, ethers, and the like. "Aqueous" with reference to solutions or solvents refers to solutions or solvents which consist primarily of water, normally greater than 90 weight percent water, and can be essentially pure water in certain circumstances. For example, an aqueous solution or solvent can be distilled water, tap water, or the like. However, an aqueous solution or solvent can include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more cosolvents, including agronomically suitable organic cosolvents, which are miscible therewith, or may form an emulsion therewith. Examples of suitable alcohol solvents include but are not limited to methanol, ethanol, propanol, isopropanol, hexanol, as well as glycols such as ethylene glycol, and the like. Examples of suitable nitriles include acetonitrile, propionitrile, butyronitrile, benzonitrile, and the like. Examples of suitable amides include formamide, N,N-dimethylformamide, N,N-dimethylacetamide, and the like. Examples of suitable esters include methyl acetate, ethyl acetate, and the like. Examples of suitable ketones include acetone, methyl ethyl ketone, diethyl ketone, and the like.

Examples of suitable ethers include diethyl ether, tetrahydrofuran, dioxane, dimethoxyethane, and the like. Any two or more of any of the foregoing solvents may be utilized in the coating composition as well. Currently preferred solvents include water, particularly distilled water, isopropanol, acetonitrile, and combinations of any two or more of these solvents.

In one preferred embodiment, the covalent complex is solubilized in solvent to achieve a concentration of between about 0.01 and about 10 percent by weight, preferably between about 0.1 and about 1 percent, and more preferably about 0.125 percent.

In addition to the foregoing solvents, the heparin coating compositions of the present invention may also include therein various conventional additives. Examples of additives which may be incorporated into the compositions of the present invention include but are not limited to benzalkonium, 4-dimethylaminopyridinium, tetrabutylammonium halides, and the like.

The coating composition may be coated onto any of a wide variety of surface materials to provide anti-thrombogenic effects when the coated surface is contacted with blood. Suitable surfaces which may be coated with the coating composition of the present invention include any surface which has an affinity or attraction to the hydrophobic silyl moiety. Such surfaces are typically hydrophobic surfaces. Examples of suitable surfaces include but are not limited to hydrophobic polymers such as polycarbonate, polyester, polypropylene, polyethylene, polystyrene, polytetrafluoroethylene, polyvinyl chloride, polyamide, polyacrylate, polyurethane, polyvinyl alcohol, polyurethane, polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steal and graphite.

The heparin coating composition can be applied to the surface to render the blood-contacting surface resistant to fibrin accumulation and resistant to cell attachment. Any suitable method for applying the coating composition to the surface may be employed. One suitable method for applying the coating composition to the blood-contacting surface to be treated is by dipping the blood-contacting surface into the coating composition containing the covalent complex of the present invention. A liquid coating composition containing the covalent complex of the present invention may be prepared using any of the solvents described above. The surface is dipped or immersed into a bath of the coating composition. Typically, the dipping process is carried out at elevated temperatures, such as between about 30° C. and about 80° C. for a period of between about 5 and about 20 minutes, preferably about 10 minutes. Thereafter, the surface is allowed to remain in contact with the coating composition containing the covalent complex for a period of between about 15–60 minutes, preferably about 20 minutes, at room temperature.

Another method that may be employed for coating or applying the heparin coating compositions of the present invention onto blood- or cell-contacting surfaces includes a pumping or spraying processes. According to the pumping process, the coating solution having a concentration of between 0.05 and about 5 percent (w/v) is pumped through the device, where the blood or cell contact will occur, for about 30 minutes. Thereafter the excess coating materials is washed out with water or saline. The blood- or cell-contacting surface can be coated by the material of the current invention simply by spraying with the above-mentioned coating solution as well. The coated surface is typically washed with water before drying.

Following coating of the composition onto the surface, the surface is typically washed with water or saline prior to drying. Advantageously, the foregoing methods for applying the coating composition to a surface are relatively quick, commercially feasible and cost-effective. They require no special equipment or special technical training, and can be applied to devices with complex surface geometries.

The hydrophobic interactions between the hydrophobic surfaces to be coated and the hydrophobic silyl moieties of the covalent complex form the bond between the covalent complex and the surface. This hydrophobic interaction is sufficiently strong so as to provide a stable bond between the covalent complex and the surface. The present inventors have now discovered a method for binding heparin to a surface by using hydrophobic binding interactions which provide certain advantages over the method relied upon in previous coating technologies. The presence of ionic species in blood does not disrupt the hydrophobic interaction between the covalent complex of the present invention and the surface.

Fibronectin Complexation

Fibronectin has known and demonstrated affinity for heparin. Fibronectins are composed of two similar protein chains, with each chain including one domain for cell binding and two domains, one at each end of the chain, for heparin binding. Affinity binding of fibronectin results in an affinity constant of approximately $10^8$ M.

Any form of fibronectin may be employed, including fibronectin derived from cells, plasma, or tissues, and may be natural or genetically engineered, and may be of human origin or derived from another animal species. Other adhesive molecules, as defined above, may also be employed, utilizing the methods described herein for fibronectin.

Following coating of the surface with a silyl-heparin complex, the fibronectin may be affinity complexed to the heparin, resulting in a silyl-heparin-fibronectin complex. To affinity complex the fibronectin, the fibronectin is solubilized in one or more solvents which facilitate the processes of applying the fibronectin composition to the silyl-heparin-coated surface. Suitable solvents will be those which at least partially solubilize fibronectin and which do not interfere with the activity of heparin or the cellular-attachment activity of fibronectin. Examples of solvents that may be employed in the present invention include aqueous solutions; aqueous solutions containing alcohols, nitriles, amides, esters, ketones, ethers, and the like; and alcohols, nitriles, amides, esters, ketones, ethers, and the like. Aqueous solutions are thought to be particularly useful for non-synthetic fibronectins and organic-based solvents for synthetic fibronectins and peptides derived therefrom. "Aqueous" with reference to solutions or solvents refers to solutions or solvents that consist primarily of water, normally greater than 90 weight percent water, and can be essentially pure water in certain circumstances. For example, an aqueous solution or solvent can be distilled water, tap water, or the like. However, an aqueous solution or solvent can include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more cosolvents, including agronomically suitable organic cosolvents, which are miscible therewith, or may form an emulsion therewith.

The fibronectin composition can be applied to the silyl-heparin-coated surface to render the blood- or cell-contacting surface suitable for cellular adhesion and attachment. Any suitable method for applying the fibronectin composition to the surface may be employed. One suitable method for applying the fibronectin composition to the silyl-heparin-coated surface to be treated is by dipping the silyl-heparin-coated surface into the fibronectin composition of the present invention. The silyl-heparin-coated surface is dipped or immersed into a bath of the fibronectin composition. Typically, the dipping process is carried out at elevated temperatures, such as between about 30° C. and about 80° C., and preferably between about 40° C. and about 50° C., for a period of between about 5 and about 60 minutes, preferably between about 20 and about 30 minutes.

Another method that may be employed for coating or applying the fibronectin compositions of the present invention on to silyl-heparin-coated surfaces includes a pumping or spraying processes. According to the pumping process, the coating solution having a concentration of between 0.05 and about 5 percent (w/v) is pumped through the device where the blood contact will occur for about 30 minutes. Thereafter the excess coating materials is washed out with water or saline. The blood-contacting surface can be coated by the material of the current invention simply by spraying with the above-mentioned fibronectin solution as well. The coated surface is typically washed with water before drying.

Following attachment of the fibronectin to the heparin of the silyl-heparin coating of the composition onto the surface, the surface is typically washed with water or saline prior to drying. Advantageously, the foregoing methods for applying the coating composition to a surface are relatively quick, commercially feasible and cost-effective.

In an alternative embodiment, the fibronectin may be complexed in an aqueous solution with silyl-heparin, and then the entire silyl-heparin-fibronectin complex attached to the medical device. In this approach, the silyl-heparin is dissolved directly in water and mixed with a predetermined amount of fibronectin such that the fibronectin is essentially entirely complexed with the silyl-heparin. To the solution is slowly added an organic solvent such as isopropanol to a concentration of between 20% and 80% and preferably about 35%. Under these conditions the silyl-heparin-fibronectin complex undergoes the formation of micelles, with the fibronectin-heparin portion of the complex sequestered on the inside of the micelle. A solution of micelles can then be applied to the surface of an appropriate material, thereby allowing the micelles to associate by hydrophobic interaction. Rinsing in an aqueous solution is used to remove excess unbound material and allow the heparin-fibronectin to associate in the aqueous phase. This approach is particularly applicable to fibronectin-derived peptide polymers.

In yet another embodiment, molecules may be employed in addition to the adhesive molecules defined above. These include, without limitation, polylysine, polyornithine, and similar molecules with net positive charges that associate with heparin by charge-charge interaction and thereby provide cell adhesive properties. Polylysine and polyornithine are known to enhance cell attachment on certain types of cell culture ware, and may be applied and bound to silyl-heparin complexes as described herein.

A variety of growth factors and cytokines can also be complexed to extracellular matrix heparin and heparan sulfate. The bound growth factors can thereby be used to promote cell adhesion by providing a display of ligands to which cell surface receptors can bind. Fibroblast growth factor (FGF), platelet-derived growth factor (PDGF), and bone morphogenic protein (BMP) are examples of growth factors that complex to heparin. Similarly, cytokines are known to interact with heparin, and cytokines, such as gamma-interferon, may be complexed to extracellular matrix heparin and heparan sulfate compositions of this invention, including the silyl-heparin substrate.

In yet another embodiment, more than one type of adhesive molecule may be complexed to silyl-heparin substrate. Thus, both a growth factor and fibronectin may be applied to silyl-heparin such that the final coating contains both types of adhesive molecules. The fibronectin is bound by integrins on the cell surface while a fibroblast growth factor, for example, is bound by its own distinct set of receptors. The bound growth factor also provides a vehicle to maximize cellular repopulation of the coated surface.

The heparin and fibronectin coating compositions of the present invention can be applied to the blood-contacting, tissue-containing, or cell contacting surfaces of any of a wide variety of medical devices to provide the medical device with one or more surfaces promoting cellular adhesion and attachment. Examples of specific medical devices which may be advantageously treated with the coating compositions of the present invention include but are not limited to artificial blood vessels, blood shunts, nerve-growth guides, artificial heart valves, prosthetics, pacemaker leads, in-dwelling catheters, cardiovascular grafts, bone replacements, wound healing devices, cartilage replacement devices, urinary tract replacements and the like. Other examples of medical devices which would benefit from the application of the cellular-adhesive coating compositions of the present invention will be readily apparent to those skilled in the art of surgical and medical procedures and are therefore contemplated by the instant invention.

The following examples are provided to illustrate the present invention, and should not be construed as limiting thereof. In these examples, "$\mu$L" means microliter, "mL" means milliliter; "L" means liter, "$\mu$g" means microgram, "mg" means milligram, "g" means gram, "mol" means moles, "M" means molar concentration, "Me" means methyl; "Bn" means benzyl, "nBu$_4$NI" means tetrabutylammonium iodide, "° C." means degrees Centigrade. All percentages are in percent by weight unless otherwise indicated.

EXAMPLE 1

Method for Preparing Silyl-Heparin Covalent Complexes

Synthesis of Benzyl(chloromethyl)dimethylsilane

In a 2 L 3-necked flask equipped with a nitrogen inlet, a 500 ml dropping funnel and a thermometer, was placed 500 ml of tetrahydrofuran. Chloro(chloromethyl)-dimethylsilane (100 ml, 0.744 mol) was added by syringe and the colorless solution cooled to 0° C. in an ice/acetone bath. Then benzylmagnesium chloride (2.0 M solution, 400 ml, 0.8 mol) was transferred to the dropping funnel by syringe and added dropwise over 2 hours. A slightly exothermic reaction was observed and the temperature was maintained below 10° C. After addition of the benzylmagnesium chloride was complete, the ice bath was allowed to warm up to room temperature without heating, and the reaction mixture was stirred overnight. Thereafter hexane (300 ml) was added and the reaction mixture was worked up by dropwise addition of saturated aqueous ammonium chloride (300 ml) and transferred to a 2 L separatory funnel with additional hexane (300 ml). After partitioning, the organic layer was washed with saturated aqueous ammonium chloride (200 ml) and saturated aqueous sodium chloride (200 ml). The combined aqueous layers were backwashed with hexane (2×500 ml). The combined organic layers were dried over magnesium sulfate, evaporated on a rotary evaporator, and finally evaporated with an oil pump to give a colorless oil 162.0 g (109.5% yield). A quantitative yield was assumed with a purity of the crude product as 91.3%.

Grignard Reaction of Bn(SiMe$_2$CH2)$_n$Cl and ClSiMe$_2$CH$_2$Cl to give Bn(SiMe$_2$CH$_2$)$_{n+1}$Cl In a 500 ml 3-necked flask equipped with a condenser-nitrogen inlet, a septum and a thermometer, was placed magnesium powder (7.5 g, 0.31 mol), a catalytic amount of iodine and tetrahydrofuran (100 ml). The brown mixture was heated to reflux briefly with a heat gun until the color of iodine disappeared. Bn(SiMe$_2$CH$_2$)$_n$Cl (0.2 mol) was added by syringe and washed down with the tetrahydrofuran (2×25 ml). The reaction was initiated with a heat gun. An exothermic reaction was observed and the reaction flask was placed in a water bath until the exothermic reaction subsided. The resulting grey mixture was heated to reflux for 24 hours. The reagent was then cooled to room temperature and cannulated into a pressure filter funnel where it was added directly into another 500 ml round bottom flask in which was placed a solution of ClSiMe$_2$CH$_2$Cl (27.0 ml, 0.2 mol) in tetrahydrofuran (50 ml) at room temperature. The magnesium residue was washed down with tetrahydrofuran (2×25 ml). The reaction mixture was heated to reflux overnight. The resulting grey suspension was worked up by addition of saturated aqueous sodium bicarbonate (50 ml) and transferred to a 500 ml separatory funnel with hexane (200 ml). After partition, the organic layer was washed with saturated aqueous sodium bicarbonate (50 ml) and saturated aqueous sodium chloride (50 ml). Then the combined aqueous layers were back-washed with hexane (2×100 ml). The combined organic layers were dried over magnesium sulfate, evaporated on a rotary evaporator and finally evaporated on the oil pump to give an amber oil, which can be purified by distillation to give a colorless oil. Yield is approximately 80 percent.

Conversion of Bn(SiMe$_2$CH$_2$)$_n$Cl to Bn(SiMe$_2$CH$_2$)$_n$OH

Bn(SiMe$_2$CH$_2$)$_n$Cl (0.16 mol) was dissolved in dimethylformamide (300 ml) in a 1 L 3-necked flask. Potassium acetate (50 g, 0.5 mol) was added followed by nBu$_4$NI (4.0 g, 0.01 mol) and the reaction mixture was stirred in a 135° C. oil bath for 24 hours. The reaction mixture was worked up by cooling to room temperature, transferred to a 1 L separatory funnel with hexane (500 ml), and washed with saturated aqueous sodium chloride (3×100 ml). The combined aqueous layers were back-washed with hexane (3×300 ml). The combined organic layers dried over magnesium sulfate, and evaporated on a rotary evaporator to give an amber oil. The oil was dissolved in methanol (400 ml). Then a generous amount of freshly prepared sodium methoxide was added to adjust the pH to >10 and the reaction mixture was heated to reflux for 2 hours. The reaction mixture was worked up by neutralizing with acetic acid (AcOH), and evaporated to dryness. The dried mixture was chromatographed with silica gel in a 6.5×100 cm (height of silica 40 cm) flash column and eluted with 0–30% ethylacetate/hexane to give the desired product as a slightly yellow oil. The yield is approximately 80 percent.

Conversion of Bn(SiMe$_2$CH$_2$)$_n$OH to Bn(SiMe$_2$CH$_2$)$_n$OCO$_2$N(COCH$_2$)$_2$ Triphosgene (60 g, 0.2 mol) was dissolved in methylene chloride (200 ml) and stirred at 0° C. under nitrogen in a 1 L 3-necked flask equipped with thermometer, dropping funnel and nitrogen inlet. Sodium carbonate (65 g, 0.6 mol) was added followed by Bn(SiMe$_2$CH$_2$)$_n$OH (0.13 mol dissolved in 200 ml methylene chloride) dropwise over 30 minutes. Thereafter, the ice/acetone bath was allowed to warm to room temperature without addition of heat. The reaction mixture was allowed to stir overnight and worked up the next morning by filtering through a sintered glass funnel, which was washed down with toluene (PhCh$_3$) (200 ml). Thereafter the filtrate was evaporated on a rotary evaporator to give a colorless oil, which was dissolved in methylene chloride and stirred in an ice bath under nitrogen. N-Hydroxysuccinimide (30 g, 0.26 mol) was added, followed by dropwise addition of triethylamine (Et$_3$N) (40 ml, 0.28 mol) over 15 minutes. The resulting cloudy mixture was stirred at room temperature for 1 hour. The reaction mixture was then worked up by diluting with hexane (600 ml), washed with saturated aqueous ammonium chloride (3×100 ml), and the combined aqueous phases backwashed with hexane (2×200 ml). The combined organic phases were dried over magnesium sulfate and evaporated to dryness on a rotary evaporator to give an amber oil. The oil was chromatographed with silica gel in a 6.5×100 cm (height of silica 40 cm) flash column and eluted with 20–50% ethyl acetate/hexane to give an amber syrup. The yield is approximately 70 percent.

Conjugation of Heparin with Bn(SiMe$_2$CH$_2$)$_n$OCO$_2$N(COCH$_2$)$_2$

Heparin (ammonium free, average molecular weight 10,000; 100 g, 10 mmol) was dissolved in 500 ml of water in a 4000 ml beaker with stirring. DMF (400 ml) was added followed by DMAP (5.0 g, 40 mmol) and the pH was monitored by a 702 SM Titrino with program set at: end pont=8.50, max flow rate=1 ml/min., min. flow rate=10 $\mu$l/min., pause time=60 sec., stop criteria=time (inf.) and connected to a reservoir of 1 M sodium hydroxide. Bn(SiMe$_2$CH$_2$)$_n$OCO$_2$N(COCH$_2$)$_2$ (10×mmol) in DMF (100 ml) was added and the pH began to drop. The program was started as soon as the pH dropped to just below 8.5. The resulting milky mixture was allowed to stir at room temperature while the pH of the reaction mixture was maintained at 8.5 by Titrino by automatic addition of 1M sodium hydroxide as necessary. The amount of 1 M sodium hydroxide used (in ml) was plotted against reaction time (in hours) as the reaction profile. The reaction mixture was worked up, when the reaction profile begins to flatten out, by trituration with acetone (2 l) and the white suspension is filtered through a sintered glass funnel to give a white solid residue, which was contaminated with DMF and some of the residual N-hydroxy-succinimide. This crude material can be purified by soxhlet extraction with acetone overnight to give a white powder. The yields are generally greater than 95%.

Procedure for Coating the Complexes Onto the Surface

The complex is completely dissolved in ⅓ volume of distilled water with gentle stirring. A solvent such as isopropyl alcohol or acetonitrile is added in the amount of ⅔ volume and the solution is mixed. The thus prepared coating solution has a complex concentration of between 0.01 and 10 percent based upon the weight of the solution. The material to be coated is dipped in the coating solution at elevated temperatures usually ranging from 30° C. to 50° C. for about 10 minutes, followed by standing in room temperature for about 20 minutes. The coated material is taken out of the coating solution and rinsed thoroughly with distilled water or saline solution prior to drying.

EXAMPLE 2

One Technique for Applying Silyl-Heparin Coating Compositions to Surfaces

The covalent complex (100 mg) produced according to Example 1 above is solubilized in ⅓ volume, 27 ml of distilled water with gentle stirring. Thereafter ⅔ volume, 53 ml of isopropyl alcohol or acetonitrile is added. The resulting concentration of the covalent complex in solution is about 0.125 percent by weight. The blood-contacting surface to be coated with the coating composition is dipped into the coating composition for 10 minutes at a temperature of between 30° C. to 50° C. Thereafter, the surface is allow to remain in contact with the coating composition for approximately 20 minutes, at room temperature. Thereafter, the coated surface is removed from the coating composition and rinsed thoroughly with distilled water or saline solution.

EXAMPLE 3

Stability of Heparin Coating Compositions on Surfaces Exposed to Ionic Environments Various surfaces coated according to Example 2 were evaluated for heparin activity after washing with 3 percent (by weight) sodium chloride solution. Surface heparin activity is measured in mlU/cm$^2$ according to the technique described in Sigma Diagnostics, Heparin, Procedure No. CRS 106.

Results obtained from the evaluation of average heparin activity on various surfaces after washing with sodium chloride are set forth in Table I below. The concentration of the covalent complex in the coating solution was 0.25% (WN).

TABLE 1

| | Percent by volume of isopropyl alcohol in IPA/H$_2$O solvent | | | | | |
|---|---|---|---|---|---|---|
| Material Coated | 50 | 55 | 60 | 65 | 70 | 75 |
| POLYCARBONATE | 6.8 | 8.0 | 17.6 | 16.3 | 14.7 | 14.9 |
| TMCTS | 0.4 | 3.8 | 3.5 | 2.0 | 1.1 | 2.4 |
| POLYESTER | 4.5 | 4.4 | 5.5 | 3.7 | 5.3 | |
| POLYVINYL CHLORIDE | 2.6 | 2.9 | 10.0 | 6.5 | 4.0 | 2.8 |
| STAINLESS STEEL | 12.9 | 13.1 | 8.3 | 11.0 | 12.9 | 13.8 |

EXAMPLE 4

Silyl-Heparin Application Prior to Fibronectin Attachment

Benzyl magnesium chloride was treated serially with chloro(chloromethyl) dimethylsilane to give a benzyl-(1,2 dimethyl)disilyl compound. The benzyldisilyl compound was modifed to form an activated succinimidyl ester that was, in turn, conjugated to heparin to form a benzyl-(1,2 dimethyl)disilyl heparin. This is shown in Scheme 2 below.

Scheme 2

The silyl-heparin was used as a 1% solution in 70% acidified, aqueous ethanol. To coat wells, the silyl-heparin solution was applied in 20 μL/well for 15 minutes at 50–60° C. The wells were then rinsed several times in saline and air-dried. To coat other compositions, the composition were immersed in the 1% silyl-heparin solution as described for 15 minutes at 50–60° C., and rinsed extensively in water or saline.

The silyl-heparin coating may be applied to any polymeric substrate, either forming a medical or other implantable device, or coated or otherwise forming a surface of a medical or other implantable device. The coating was applied, as described, to polystyrene and polyurethane polymeric surfaces. The polymeric substrate includes biodegradable polymers, including, for example, polylactide, polylactide:polyglycolide and polycaprolactone, to which the silyl-heparin coating was applied. The silyl-heparin coating may also be applied to any metallic substrate, and was applied to stainless steel.

EXAMPLE 5

Attachment of Fibronectin to Silyl-Heparin Coated Substrate

Fibronectin was attached to the silyl-heparin coated substrates of Example 4 by incubation of in an aqueous 0.9% saline solution and 20 μg/mL bovine plasma fibronectin. After 30 minutes the unbound fibronectin was rinsed off. The silyl-heparin-fibronectin coated substrates were then either used directly or air dried and stored for subsequent use.

EXAMPLE 6

Detection of Heparin and Fibronectin

Using surfaces coated with silyl-heparin as in Example 4, and to which fibronectin was attached as in Example 5, the presence of both heparin and fibronectin was detected in analytical assays. Heparin was detected using a commerically-available an enzyme-linked assay kit (Sigma Chemical Co., St. Louis) that measures the heparin-induced inhibition of antithrombin/factor Xa as measured with a factor Xa specific chromogenic substrate. The enzyme-inhibition assay was performed in low-attachment 96 well plates following the directions of the manufacturer.

To insure that the amphipathic heparin did not introduce an unknown variable in the enzyme inhibition assay, a second assay was performed using a hydrazine-activated biotin (Yu and Toole, 1995). These assays were performed in low-attachment 96 well plates. A solution of hydrazine-activated biotin was added to wells that were uncoated or coated with silyl-heparin. The solution was composed of 0.1 M sodium acetate, pH 5.2, containing 350 g of EZ-link biotin-LC-hydrazine (Pierce Chemical Co.). After 30 minutes, the wells were rinsed in water and quenched in 5% dextrose. A solution of PBS containing 20% serum and a 1:1000 dilution horseradish peroxidase-conjugated avidin (HRPO-avidin) was added. After 30 minutes the unbound material was rinse off and a chromogenic solution of ABTS (1-Step ABTS, Pierce Chemical Co.) added. Upon color development, an aliquot of 0.2 M sulfuric acid was added to stop the reaction, and the absorbance detected at 650 nm.

Fibronectin was detected immunochemically. The assays were performed in low-attachment 96 well plates in wells with no coating, a coating of fibronectin, or a coating of silyl-heparin/fibronectin. PBS containing a saturating amount of gelatin and rabbit anti-human fibronectin (known to be cross-reactive with bovine fibronectin) was added to the wells. After 30 minutes the primary antibody was removed, the plate rinsed, and a solution of PBS containing a saturating amount of gelatin and goat anti-rabbit IgG was added. After 30 minutes the unbound material was rinsed off and a chromogenic solution of ABTS (1-Step ABTS, Pierce Chemical Co.) added. Upon color development, an aliquot of 0.2 M sulfuric acid was added to stop the reaction, and the absorbance detected at 650 nm.

EXAMPLE 7

Cells Used for Adhesion Studies

Several cell types were used, including GS-9L cells (rat gliosarcoma), C3H10T1/2 (murine fibroblasts), Jurkat (human T cell), bovine aorta endothelial (BAE) cells and rat lymphocytes. GS-9L and C3H10T1/2 were maintained in log phase growth and detached from cultureware using Versene and collected by centrifugation. Jurkat cells grew as single cell suspensions and were collected by centrifugation. Rat lymphocytes were collected from heparinized blood by density gradient isolation over Ficoll-Hypaque® media. The collected cells were rinsed once by low speed centrifugation and suspended in either serum-free Dulbecco's Modified Eagles Medium (DMEM) containing pyruvate or RPMI 1640 containing 10% fetal bovine serum supplemented with pyruvate. Aliquots of $10^4$ cells in 100 μL were used in subsequent adhesion studies.

The cells were examined after plating using an inverted, phase-contrast microscope. At selected time points up to 4 days after initial seeding, the cells were rinsed three times in saline and fixed in buffered 10% formalin or 35% ethanol. In some cases, the cells were stained in situ with a 0.01% aqueous solution of crystal violet. The amount of attachment was scored visually or quantitated. To establish the relative number of cells bound, crystal violet stained cells were dissolved in a solution of 70% ethanol containing 0.1% sodium dodecyl sulfate and 0.38 M Tris and the absorbance monitored at 610 nm, using the methods of Scragg and Ferreira (*Anal Biochem* 198:80–5, 1991) and Grando et al.(*Skin Pharmacol* 6:135–47, 1993).

EXAMPLE 8

Attachment of Cells

The cells of Example 7 were added to untreated polystyrene wells, wells coated with silyl-heparin as in Example 4, with silyl-heparin-fibronectin as in Example 5, and with only fibronectin by incubation as described in Example 5. As shown in Table 2, C3H10T1/2 fibroblasts, GS-9L gliosarcoma, Jurakt T cells, BAE cells and rat lymphocytes cultured in serum-containing medium on low-attachment, nominally non-adherent polystyrene did not attach to the substrate. Similarly, these cells cultured on silyl-heparin alone did not attach. When seeded following pre-treatment with bovine fibronectin, isolated C3H10T1/2 cells and isolated GS-9L cells were found attached. When cells were cultured on silyl-heparin-fibronectin, CH310T1/2, BAE and GS-9L cells rapidly attached and spread onto the substrate. Cells were seeded at a concentration of $10^4$ cells/well in serum-containing medium.

hours nearly all of the cells evidenced spreading. The morphology of GS-9L, C3H10T1/2 and BAE cells after 24 hours on silyl-heparin-fibronectin were similar to cells grown on conventional tissue cultureware. The cells grew to confluency by 4 days. Cells seeded in serum-free medium attached and spread although not as well as in serum-containing medium, and further did not grow. No effort was made to grow the cells in a defined- or serum-low medium known to support growth. Addition of up to 10 U of heparin to the medium of cells plated onto silyl-heparin-fibronectin coated plates did not inhibit the attachment or growth of C3H10T1/2. The results for C3H10T1/2 cells are shown in Table 3.

TABLE 3

| | CHARACTERISTIC | | |
| --- | --- | --- | --- |
| | ATTACHMENT | SPREADING | GROWTH |
| GS-9L CELLS | | | |
| Serum | ++++ | ++++ | ++++ |
| Serum-free | +++ | +++ | – |
| C3H10T½ CELLS | | | |
| Serum | ++++ | ++++ | ++++ |
| Serum-free | +++ | +++ | – |

EXAMPLE 10

Use on Variety of Substrates

The general applicability of silyl-heparin/fibronectin was evaluated by applying this coating using the methods of Examples 4 and 5 to a variety of surfaces, including polystyrene, polylactide:polyglycolide, polycaprolactone, polurethane, and stainless steel. As in Example 9 above, C3H10T1/2 cells did not attach to polystyrene. C3H1OT1/2 cells also did not attach to polyurethane. They did, however, bind moderately well to polylactide:polyglycolide and to polycaprolactone, and very well to stainless steel. Regardless of the substrate, coating with silyl-heparin essentially eliminated cell attachment. The inhibition of cell attachment was noted even on surfaces known to support cell growth, such as stainless steel. Even when the cells were culture for up to 4 days, no cell attachment was evident. Treating the plates with heparin alone did not inhibit attachment. Fibronectin alone did not significantly support cell attach-

TABLE 2

| | CELL ATTACHMENT | | | |
| --- | --- | --- | --- | --- |
| CELL TYPE | UNTREATED | SILYL-HEPARIN | FIBRONECTIN | SILYL-HEPARIN-FIBRONECTIN |
| GS-9L | – | – | +/– | ++++ |
| C3H10T½ | – | – | +/– | ++++ |
| BAE | – | +/– | – | +++ |
| Jurkat | – | – | – | – |
| Lymphocytes | – | – | – | +/– |

EXAMPLE 9

Adherence and Cell Spread

Using the methods as described in Example 8, GS-9L, C3H10T1/2 and BAE cells were adhered by 1 hour after seeding on silyl-heparin-fibronectin, and many of the cells demonstrated evidence of spreading onto the substrate. By 2 ment to polystyrene. It did, however, improve the attachment of cells to polyurethane and polylactide:polyglycolide, and to a lesser extent polycaprolactone. Silyl-heparin-fibronectin increased the cell density for all substrates relative to the uncoated surfaces, and increased the cell density on polycaprolactone by about 2 fold. The results are summarized in Table 4.

TABLE 4

| | C3H10T ½ CELL ATTACHMENT | | | |
|---|---|---|---|---|
| SURFACE | UNTREATED | SILYL-HEPARIN | FIBRONECTIN | SILYL-HEPARIN-FIBRONECTIN |
| Polystyrene | − | − | −/+ | ++++ |
| Polyurethane | − | − | ++++ | ++++ |
| Polyactide:polyglycolide | ++ | − | ++++ | ++++ |
| Stainless steel* | ++++ | − | ++++ | ++++ |
| Polycaprolactone* | +/− | +/− | ++ | ++++ |

*determined by crystal violet staining

EXAMPLE 11

Determination of Optimal Concentrations of Fibronectin and Silyl-Heparin

Figure 1:
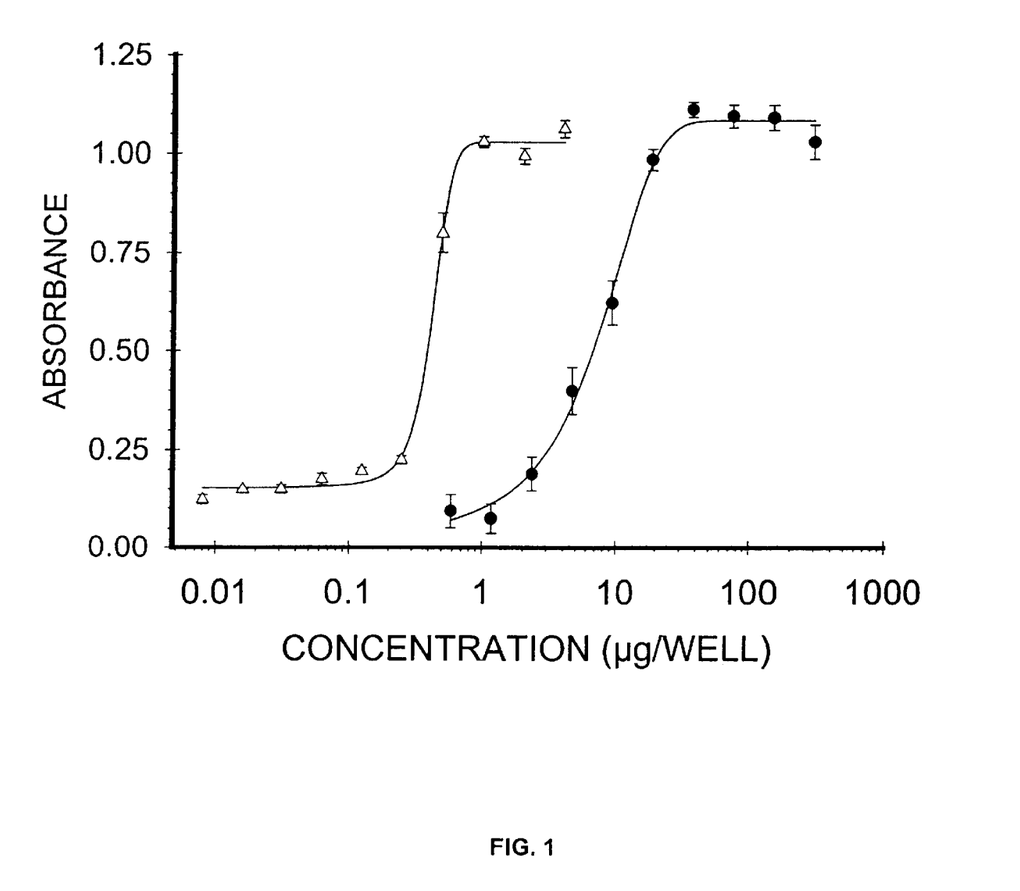
FIG. 1 is a titration plot of the amount of fibronectin and silyl-heparin needed to support cell attachment.

The optimal amount of fibronectin and s-heparin to support attachment of C3H10T1/2 cells was determined by cross-titration, as shown on FIG. 1. The $EC_{50}$ for fibronectin was approximately 0.5 µg/well and that of s-heparin about 8.7 µg/well. The cell attachment curve for the fibronectin dilution had a rapid fall-off, suggestive of a threshold effect. The fall-off for the silyl-heparin was more gradual. The curve of the relative amount of silyl-heparin on the substrate following serial dilution generally followed the cell attachment curve. The curve of the relative amount of fibronectin bound to silyl-heparin did not mirror the cell attachment curve.

In FIG. 1, fibronectin (Δ - - - Δ) or silyl-heparin (• - - - •) were titrated to determined the quantity needed to support attachment of C3H10T1/2 cells. All dilutions were performed in quadruplicate in wells of 96-well plates of low-attachment polystyrene. All dilutions were performed in quadruplicate in wells of 96-well plates of low-attachment polystyrene. For titration of fibronectin, silyl-heparin was applied at 30 µg/well in 70% ethanol as in Example 4. After rinsing, fibronectin was applied in doubling dilutions of phosphate buffered saline starting from 4 µg/well. For titration of silyl-heparin, silyl-heparin was applied in doubling dilutions in 70% ethanol starting from silyl-heparin concentrations of 30 µg/well. Fibronectin was then applied in saline at 4 µg/well. Cells were at a concentration of $10^4$ cells/well in growth medium. For both experiments, the cells were allowed 24 hours to attach and then were rinsed and fixed in buffered formalin. The cells were stained for 5 minutes with 0.01% aqueous crystal violet and the absorbance at 610 nm determined.

Figure 2:
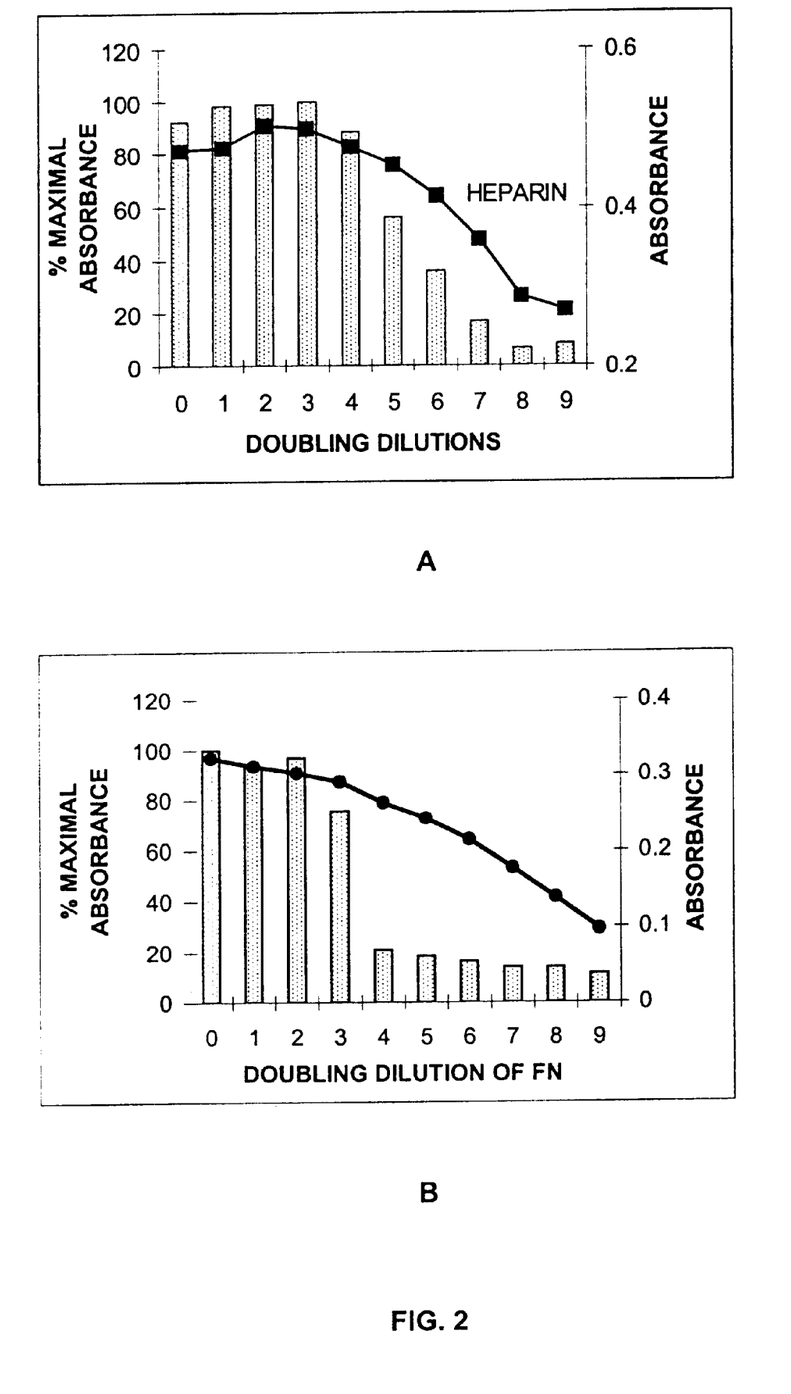

FIG. 2 compares the relative amounts of bound heparin and fibronectin in doubling dilutions to attached cell density. In FIG. 2A the relative amount of bound heparin was compared to subsequent attached cell density following complexation with fibronectin (4 µg/well). In FIG. 2B the relative amount of bound fibronectin (FN) to wells precoated with silyl-heparin (300 µg/well) was compared to subsequent cell density obtained after fibronectin complexation. Cell density was expressed as the percent maximal absorbance of crystal violet. Heparin was detected using an enzyme-linked assay while fibronectin was detected immunochemically.

EXAMPLE 12

Use of Other Adhesive Molecules

Laminin was attached to the silyl-heparin coated substrates of Example 4 by incubation in an aqueous 0.9% saline solution containing 20 µg/mL intact murine laminin. After 30 minutes the unbound laminin was removed by rinsing. In studies similar to those in Example 8, C3H10T1/2 cells attached to surfaces coated with the silyl-heparin-laminin complex.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A silyl and heparin covalent composition of Formula 1:

wherein
 $R_1$ is a $C_{1-8}$ alkyl or $C_{6-32}$ aryl group,
 each $R_2$ is independently selected from the group consisting of $C_{1-8}$ alkyl and $C_{6-32}$ aryl,
 $R_3$ is N or O,
 n is a number from 1 to 10, and
 x is a number from 1 to 30.

2. The composition according to claim 1, wherein x is 1.

3. The composition according to claim 1, wherein x is from 2 to 25, whereby from 2 to 25 hydrophobic silyl moieties are covalently bound to one heparin molecule.

4. The composition according to claim 1, wherein $R_1$ is benzyl.

5. The composition according to claim 1, wherein each $R_2$ is an alkyl.

6. The composition according to claim 1, wherein n is 2 or 3.

7. The composition according to claim 1, which is [benzyl-tris(dimethylsilylmethyl)]-(N-heparinyl)-carbamate.

8. The composition according to claim 1, which is [benzyl-tris(dimethylsilylmethyl)]-(N-heparinyl)-carbamate.

9. The composition according to claim 1, which is dodecyl [benzyl-tris(dimethylsilylmethyl)]-(N-heparinyl)-carbamate.

10. The composition according to claim 1, wherein said heparin is a salt of heparin.

11. The composition according to claim 10, wherein said salt of heparin is selected from the group consisting of sodium heparin, calcium heparin, magnesium heparin and potassium heparin.

12. The composition according to claim 1, wherein said heparin is a derivative of heparin.

13. The composition according to claim 12, wherein said derivative of heparin is selected from the group consisting of ammonium heparin and benzalkonium heparin.

14. The composition according to claim 1, wherein $R_3$ is N, whereby attachment to the heparin molecule is through an amine of heparin.

15. The composition according to claim 1, wherein $R_3$ is O, whereby attachment to the heparin molecule is through a hydroxyl group of heparin.

* * * * *